United States Patent [19]

Colby et al.

[11] 4,166,909

[45] Sep. 4, 1979

[54] PROCESS FOR PREPARATION OF A SUBSTITUTED TRIAZINE

[75] Inventors: Thomas H. Colby; Ernest R. Freitas; William R. Durland, all of Houston, Tex.

[73] Assignee: Shell Oil Company, Houston, Tex.

[21] Appl. No.: 871,656

[22] Filed: Jan. 23, 1978

[51] Int. Cl.$^2$ .......................................... C07D 251/50
[52] U.S. Cl. ................................................ 544/204
[58] Field of Search ........................................ 544/204

[56] References Cited

U.S. PATENT DOCUMENTS

| | | | |
|---|---|---|---|
| 3,639,399 | 2/1972 | Daugherty et al. | 544/204 |
| 4,054,739 | 10/1977 | Haschke et al. | 544/204 |
| 4,058,662 | 11/1977 | Haschke et al. | 544/204 |

*Primary Examiner*—John M. Ford

[57] ABSTRACT

An improved process is disclosed for the preparation of 2-chloro-4-ethylamino-6-isopropylamino-s-triazine wherein two of the three chlorine atoms on cyanuric chloride are replaced with ispropylamino and ethylamino substituents by sequential reaction of cyanuric chloride in a mixed acetone/water solvent system with isopropylamine and ethylamine, respectively, in the presence of an alkali metal hydroxide acid acceptor. In this improved process, the formation of undesired 2-chloro-4,6-bis(ethylamino)- and 2-chloro-4,6-bis(isopropylamino)-s-triazine impuritiesis minimized by carrying out the initial chloride replacement reaction with an excess of cyanuric chloride over the stoichiometric amount and subsequently treating the reaction product from this initial chlorine replacement reaction with sufficient base to convert the unreacted cyanuric chloride to a water soluble basic salt of monohydroxydichloro-s-triazine followed, optionally and preferably, by phase separation of the aqueous solvent phase to remove at least a portion of the basic salt of monohydroxydichloro-s-triazine from the reaction mixture prior to the second chlorine replacement reaction.

7 Claims, No Drawings

PROCESS FOR PREPARATION OF A SUBSTITUTED TRIAZINE

BACKGROUND OF THE INVENTION

This invention relates to an improved process for preparation of 2-chloro-4-ethylamino-6-isopropylamino-s-triazine otherwise known as atrazine herbicide. More particularly, this invention is directed to an improvement on the conventional process for preparing atrazine by stepwise replacement of chlorine atoms on cyanuric chloride in a mixed water/acetone solvent system in which the purity of the desired 2-chloro-4-ethylamino 6-isopropylamino-4-triazine is held at a high level by minimizing the formation of 2-chloro-4,6-bis(alkylamino)-s-triazine impurities in the process.

2-Chloro-4-ethylamino-6-isopropylamino-s-triazine is well known in the agricultural field, under the trade name atrazine, as a selective herbicide for weed control among cultivated crops, especially corn. Although other synthetic routes are possible, much, if not all, of the commercial scale atrazine production is based on the stepwise replacement of chlorine atoms on cyanuric chloride with the appropriate alkyl amines in the presence of an acid acceptor, typically an alkali metal hydroxide. In fact, the patent art is replete with a variety of disclosures or suggestions of ways to modify and/or optimize this basic reaction scheme to obtain alkyl amino substituted s-triazine herbicides such as atrazine in high yield and purity e.g. see U.S. Pat. Nos. 3,376,302; 3,436,394; 3,586,679; 3,590,040; 3,639,399 and 3,883,515. According to these previous patent disclosures, a variety of solvent systems ranging from mixed aqueous/organic to anhydrous organic solvents can be suitably used in preparing the desired substituted triazine herbicide from cyanuric chloride. A particularly advantageous solvent system for the stepwise reaction scheme, at least from the standpoint of availability and handling ease, is a mixed acetone and water solvent system such as is disclosed in U.S. Pat. No. 2,891,855.

While the state of the art on the synthesis of substituted alkylamino-s-triazine herbicides from cyanuric chloride is rather advanced, as is evidenced by the above-mentioned patent disclosures, commercial scale production units for such triazine herbicides are not devoid of problems. One source of continuing problems is the occurrence of side reactions in the triazine synthesis which lead to alkylamino substituted s-triazine by-products in the desired triazine product. These triazine by-products must generally be held to rather low levels in the final product to assure consistent biological performance and handling properties in the field. In this regard, at least one type of substituted triazine by-product i.e. tris(alkylamino)-s-triazine, has received considerable attention, with several techniques being suggested e.g., U.S. Pat. Nos. 3,681,335; 3,681,337 and 3,705,156, to avoid or suppress its formation. In the case of 2-chloro-4-ethylamino-6-isopropylamino-s-triazine or atrazine, there are at least two other alkylamino substituted s-triazine by-products which cause considerable concern. These two by-products i.e., 2-chloro-4,6-bis(ethylamino)-s-triazine and 2-chloro-4,6-bis(isopropylamino)-s-triazine are themselves active herbicides and, as a result, it is generally necessary to restrict the quantity of each to a very low level in the final product to avoid possible performance problems in practical use situations. Typically, the specification for technical atrazine requires that neither one of these impurities exceed one percent by weight of the technical product. As a general matter, this impurity specification can be met by carefully controlling the molar charge ratio of cyanuric chloride and alkylamine i.e. ethylamine and isopropylamine, reactants at, or very close to, the stoichiometric ratio for the two reactions i.e. 1 to 1 mole ratio of alkylamine to cyanuric chloride or dichloro intermediate. While this measure of control is possible on the laboratory scale and with certain solvent systems and reaction techniques on a larger scale, it is very difficult to obtain adequate control and mixing on a commercial scale, especially with the mixed acetone/water solvent system, to insure that specification atrazine can be consistently produced. The use of a small molar excess of isopropylamine in the first stage of the synthesis invariably leads to the formation of excessive amounts of 2-chloro-4,6-bis(isopropylamino)-s-triazine whereas charging less than the stoichiometric amount of isopropylamine gives rise to the formation of excessive quantities of 2-chloro-4,6-bis(ethylamino)-s-triazine in the second reaction stage. Deviations as small as 3–5% from the stoichiometric ratio in the first reaction stage can lead to the formation of excessive amounts of either of these impurities depending on the reaction conditions and technique selected.

From the foregoing, it is apparent that it would be extremely advantageous if a technique could be developed whereby the formation of 2-chloro-4,6-bis(ethylamino)-and-4,6-bis(isopropylamino)-s-triazine could be minimized in the synthesis of 2-chloro-4-ethylamino-6-isopropylamino-s-triazine from cyanuric chloride without requiring that the molar charge ratio of cyanuric chloride to alkylamine reactant be maintained within impractically narrow limits.

SUMMARY OF THE INVENTION

A surprisingly effective technique has now been found for minimizing the formation of 2-chloro-4,6-bis-(ethylamino)-and-4,6-bis(isopropylamino)-s-triazines in the synthesis of 2-chloro-4-ethylamino-6-isopropylamino-s-triazine by sequential substitution of isopropylamine and ethylamine on cyanuric chloride in the presence of an alkali metal hydroxide acid acceptor and a mixed acetone/water solvent. In this improved process, the conventional stepwise reaction scheme is modified such that the initial reaction between isopropylamine and cyanuric chloride is carried out using an excess of cyanuric chloride over the stoichiometric amount and the unreacted excess cyanuric chloride in the reaction product is subsequently base hydrolyzed to a water soluble basic salt of monohydroxydichlorotriazine before the reaction mixture is passed to the second reaction stage. The use of base catalyzed hydrolysis in this modified reaction scheme is quite advantageous, as contrasted for example, to acid catalyzed hydrolysis, because of the faster reaction rates achievable and the reduced make of other hydrolysis by-products which are prevalent at highly acidic pH's. In fact, with the hydrolysis technique of the present invention, it is possible to hydrolyze a substantial quantity e.g., up to 90%, of the excess cyanuric chloride in reaction times of 2 hours or less without causing significant hydrolysis of the desired 2,4-dichloro-6-isopropylamino-s-triazine intermediate. Further, the resulting basic salt of monohydroxydichlorotriazine which is formed by hydrolysis in the presence of a base remains substantially in the aqueous phase of the mixed solvent system and has no apparent adverse effect on the subsequent synthesis step, in terms of product yield or purity. This favorable partitioning of the basic salt, in turn, opens up another advantage for the invention since it can be at least partially rejected by simple phase separation thus reducing the possibility of product contamination.

Accordingly, in its broadest aspects, the present invention provides an improved process for the preparation of 2-chloro-4-ethylamino-6-isopropylamino-s-triazine by sequential reaction of cyanuric chloride with isopropylamine and ethylamine in the presence of an alkali metal hydroxide acid acceptor and a mixed acetone/water solvent system, characterized by the improvement which comprises; carrying out the initial reaction between cyanuric chloride and isopropylamine with at least a 4% molar excess over the stoichiometric amount of cyanuric chloride and subsequently treating the reaction product of this initial reaction with sufficient base e.g. alkali metal hydroxide, to afford a pH in the reaction product of between about 6 and 11 thereby hydrolyzing excess cyanuric chloride present in the reaction product to a basic salt of monohydroxydichlorotriazine before the reaction product is passed to the second reaction stage. It will be appreciated that the lower end of the pH range recited for the base promoted hydrolysis according to the invention i.e. pH of about 6, actually falls marginally on the acid side. Hydrolysis at such a low pH, although technically under acid conditions, is consistent with the principles and purpose of the invention since base must be added to the reaction mixture to maintain the pH at even this marginally acidic value in view of the highly acidic nature of the free monohydroxydichlorotriazine which is generated by hydrolysis. Thus at pH 6, the highly acidic monohydroxydichlorotriazine is substantially in the form of a basic salt and the benefits of the invention, including high reaction rates, selective hydrolysis and favorable partitioning between aqueous and non-aqueous solvent phases are all achievable.

In a preferred aspect of the present invention, at least a portion of the basic salt of monohydroxydichlorotriazine formed by hydrolysis according to the invention is removed from the reaction product prior to its passage to the second reaction stage by effecting a phase separation of the aqueous phase which forms from the mixed acetone/water solvent system during the initial reaction between cyanuric chloride and isopropylamine and the subsequent hydrolysis reaction. In this manner, a significant portion of the basic salt of monohydroxydichlorotriazine e.g. up to about half, can be easily removed from the reaction system thus minimizing the more difficult separation problems encountered after the completion of the synthesis reaction scheme when the bulk of the desired 2-chloro-4-ethylamino-6-isopropylamino-s-triazine is present as a solid precipitate.

DESCRIPTION OF THE PREFERRED EMBODIMENTS

The improvement according to the invention finds application in the conventional process for preparation of 2-chloro-4-ethylamino-6-isopropylamino-s-triazine or atrazine by stepwise amination of cyanuric chloride with isopropylamine and ethylamine in the presence of an alkali metal acid acceptor and a mixed solvent system comprising acetone and water. In this conventional process, which may be carried out using batch or continuous techniques, cyanuric chloride is initially reacted with isopropylamine to form a 2,4-dichloro-6-isopropylamino-s-triazine intermediate and this intermediate is subsequently reacted, without purification or other treatment, with ethylamine to form the desired product; both reactions being carried out in the presence of added alkali metal hydroxide acid acceptor and a mixed acetone/water solvent system which is common to both reactions. The mixed acetone/water solvent system employed in this conventional process typically contains from about 60 to about 90% by weight acetone, although the exact solvent composition may vary between reaction stages depending on the amount of water added in with the alkali metal hydroxide acid acceptor. The alkali metal hydroxide acid acceptor, which is preferably sodium hydroxide, is conveniently added as an aqueous solution e.g. 15-30% by weight sodium hydroxide. This acid acceptor functions as a sink for the chlorine released in the amination reactions, and therefore; it is essential that it be present in a molar amount at least equal to the moles of cyanuric chloride and/or alkylamine reactants (whichever is less) present in order for the reactions to go to completion. In the mixed acetone/water solvent system, the proper quantity of acid acceptor can be readily maintained by controlling the pH of the reaction system, via alkali metal hydroxide addition, at about 8 to 9 in both reaction stages. Both amination reactions may be suitably carried out at atmospheric pressure but are preferably conducted at reduced pressure e.g., 100-500 mm Hg. At these reduced pressures, the reaction temperatures suitably range between about 5 and about 60° C. with temperatures in the range of 10°-15° C. being preferred for the initial reaction and temperatures between 35° C. and 50° C. being preferred for the second amination reaction. Under these conditions the initial amination reaction is usually completed in 1 to 4 hours while the second reaction goes to completion in 0.5 to 6 hours.

In conventional practice, the molar ratios of cyanuric chloride to isopropylamine and dichlorotriazine intermediate to ethylamine in the two reactions are typically maintained at or approaching the stoichiometric ratio i.e. 1.0, in both reactions. In fact, as is pointed out above, previous practice has relied on very close control of the reactant molar ratio at stoichiometric in the first reaction stage as the primary means of controlling the 2-chloro-4,6-bis(ethylamino)-and-4,6-bis(isopropylamino)-s-triazine by-product formation within tolerable limits over the stepwise amination scheme. With the improvement according to the invention, this requirement for close control of the reactant molar ratio in the first reaction step is somewhat relaxed since any excess reactant i.e., cyanuric chloride, is converted to a nonreactive entity by the process according to the invention before it has the opportunity to enter into the by-product forming reactions. According to the invention, it is essential that cyanuric chloride be added to the initial amination reaction in a molar amount which is sufficient to preclude the formation of excessive amounts of by-product 2-chloro-4,6-bis(isopropylamino)-s-triazine in this first reaction stage. This objective is suitably achieved if cyanuric chloride is added to the first reaction stage in at least a 4% molar excess over that required to satisfy the stoichiometry of the amination reaction i.e., cyanuric chloride/isopropylamine molar ratios of at least 1.04. While no critical upper limit exists for the stoichiometric excess of cyanuric chloride employed in this initial reaction, it is preferred to maintain the cyanuric chloride/isopropylamine molar charge ratio between about 1.04 and about 1.08 to avoid excessive reaction times and losses of cyanuric chloride. After applying the improvement according to the invention, the second amination reaction i.e., the reaction between 2,4-dichloro-6-isopropylamino-s-triazine and ethylamine, is quite suitably carried out according to conventional practice using molar ratios of triazine intermediate to ethylamine which approximate the stoichiometric ratio for the reaction. Preferably, this second amination reaction is carried out using a slight stoichiometric excess of ethylamine i.e., 2,4-dichloro-6-isopropylamino-s-triazine/ethylamine molar charge ratios of about 0.95 to about 1, to promote shorter reaction times and more complete conversion of the triazine intermediate.

The excess cyanuric chloride in the reaction product from the initial amination is converted in accordance with the invention to a basic salt of monohydroxydichlorotriazine by treating the reaction product with a base under conditions which promote the basic salt formation without significant degradation of the desired triazine intermediate. This hydrolysis reaction can be carried out in a batch system or continuously, depending on the technique selected for the overall process scheme, by contacting the reaction product in the mixed acetone/water solvent in the same or different reaction vessel with an alkali or alkaline earth metal hydroxide at a reaction time and temperature sufficient to effect substantial conversion of the unreacted cyanuric chloride to the hydroxytriazine salt. The base employed for this hydrolysis reaction is preferably an alkali metal hydroxide and most preferably sodium hydroxide. The base can be added to the reaction product in any convenient manner, but is preferably introduced as an aqueous solution i.e., 15–30% by weight aqueous sodium hydroxide solution. The amount of base employed should be at least sufficient to react on an equal molar basis with the excess cyanuric chloride and preferably is used at a slight excess over that required to effect complete conversion of the excess cyanuric chloride present. In the mixed acetone/water solvent system, the desired quantity of base can be readily maintained by controlling the pH of the reaction product at between about 6 and about 11, and preferably between about 7 and about 10, via addition of base during the hydrolysis reaction. The hydrolysis reaction is suitably carried out at or near atmospheric pressure at a reaction temperature ranging from about 35° C. to about 50° C. Under these conditions, substantially complete hydrolysis of the unreacted cyanuric chloride is obtained in reaction times ranging from about 0.5 to about 2 hours.

Upon completion of the hydrolysis reaction step in accordance with the invention, the reaction product containing the basic salt of monohydroxydichlorotriazine can be passed directly in the mixed acetone/water solvent to the second amination reaction to complete the synthesis of 2-chloro-4-ethylamino-6-isopropylamino-s-triazine. Alternatively and preferably, the reaction product from the hydrolysis step is subject to a phase separation step to remove at least a portion of the water soluble basic salt of monohydroxydichlorotriazine as a component of the aqueous phase which separates from the mixed acetone/water solvent system at this stage of the stepwise synthesis scheme. This preferred aspect provides a relatively simple and economic means of removing a significant portion i.e., up to about 50%, of the hydroxytriazine hydrolysis product by taking advantage of the partial immiscibility of solvent phases which occurs primarily as a result of amination reaction product i.e. chloride salt and triazine intermediate, build up in the mixed solvent system. This phase separation can be carried out on a batch basis or continuously and is preferably effected by passing the hydrolysis reaction product to a separate vessel sized to provide sufficient residence time for complete separation of the phases. Suitable conditions for this phase separation step include temperatures of from about 25° to about 50° C. and pressures ranging from atmospheric to 5 psig. Under these conditions, complete separation of the aqueous or brine phase is generally obtained in 10 to 20 minutes. The aqueous or brine phase which separates as the lower phase in the phase separation vessel will typically contain a minor amount of acetone e.g., 10–20% by weight of the separated phase. Further, from 20 to 50% of the water originally present remains in the acetone phase which accounts for the less than complete removal of basic salt of monohydroxydichlorotriazine which is obtained in this step of the process. After removal of the separated aqueous phase as a bottoms product from the phase separation vessel, the organic or acetone phase is cooled down to the temperature desired for the second stage amination reaction and maintained at a pH of between 8 and 9 to avoid hydrolysis of the 2,4-dichloro-6-isopropylamino-s-triazine intermediate prior to its reaction with ethylamine. The separated acetone or organic phase from the optional phase separation step typically contains 5 to 15% by weight water based on the total weight of solvent present and therefore can be used directly in the second amination reaction step without adding make up water, especially where the acid acceptor is added for the second reaction as an aqueous solution.

The improvement according to the invention in minimizing the formation of 2-chloro-4,6-bis(ethylamino)- and 2-chloro-4,6-bis(isopropylamino)-s-triazine in the synthesis of 2-chloro-4-ethylamino-6-isopropylamino-s-triazine will be further described by the following illustrations which are not to be construed as limiting the invention.

ILLUSTRATIVE EMBODIMENT I

A. Not According to the Invention

A batch reaction synthesis of 2-chloro-4-ethylamino-6-isopropylamino-s-triazine was carried out in a mixed acetone/water solvent (45% by weight acetone) using a slight stoichiometric excess of cyanuric chloride in the first reaction step i.e., 1.02 mole ratio of cyanuric chloride/isopropylamine, and a molar excess of ethylamine in the second reaction step i.e., 0.95 mole ratio of 2,4-dichloro-4-isopropylamino-s-triazine/ethylamine assuring complete conversion to the triazine intermediate in the first reaction step. The stepwise synthesis was conducted in a 2,000 ml reactor equipped with an agitator and efficient baffle by initially charging acetone (400 g) cyanuric chloride (176.4 g or 0.956 moles) and isopropylamine (55.7 g or 0.947 moles) to the reactor and subsequently adding 20% aqueous sodium hydroxide (188.4 g) over a period of 45 minutes at a reaction temperature and pressure of 10° C. and 760 mm Hg, respectively. At the end of the 20% aqueous sodium hydroxide addition, the pH of the reaction mixture was 8.0. After being given an additional 20 minute reaction time at 10° C. under agitation, ethylamine (66.0 g or 0.996 moles) was added as a 68% by weight aqueous solution and the temperature of the reactor was increased to 35° C. Subsequently 156.4 g of 20% by weight aqueous sodium hydroxide was added to the agitated reactor over a period of 40 minutes while maintaining the reactor at a temperature of 35° C. and pressure of 760 mm Hg. After being given an additional 35 minute reaction time at a terminal pH of 8.5 the reactor was cooled and the product was precipitated by the addition of 1.2 liters of water. There was obtained 188.6 g of crude product. Analysis of this product via liquid chromatography gave the following composition.

| Component | Percent by Weight |
| --- | --- |
| 2-chloro-4-ethylamino-6-isopropylamino-s-triazine | 92.3 |
| 2-chloro-4,6-bis(ethylamino)-s-triazine | 1.52 |
| 2-chloro-4,6-bis(isopropylamino)-s-triazine | 0.59 |

B. According to the Invention

The general procedure described above under (A) was repeated with the following modifications in accordance with the invention. Firstly, the relative quantities of reactants added to the first reaction were altered to give a molar excess of cyanuric chloride i.e. a cyanuric chloride/isopropylamine molar ratio of 1.04, in the first amination reaction. Secondly, the reaction product from the first amination reaction containing excess, unreacted cyanuric chloride was subject to base hydrolysis prior to addition of the ethylamine reactant for the second amination reaction. This hydrolsis reaction was carried out in the same reaction vessel as was used for the amination reactions by adding sufficient sodium hydroxide, as a 20% by weight aqueous solution, to maintain the pH at 10.5 for a reaction time of 30 minutes at a reaction temperature of 35° C. Upon completion of the hydrolysis reaction period, the second amination reaction was carried out as above and water added to afford a crude product analyzing as follows:

| Component | Percent by Weight |
| --- | --- |
| 2-chloro-4-ethylamino-6-isopropylamino-s-triazine | 98.6 |
| 2-chloro-4,6-bis(ethylamino)-s-triazine | 0.91 |
| 2-chloro-4,6-bis(isopropylamino)-s-triazine | 0.25 |

ILLUSTRATIVE EMBODIMENT II

A 22% by weight solution of cyanuric chloride in acetone was introduced to a continuous reactor consisting of two back mixed stages. Less than the stoichiometric amount of isopropylamine was added to the reactor system, e.g. the molar ratio of cyanuric chloride/isopropylamine was 1.05. Sufficient sodium hydroxide was added as a 20% weight aqueous solution to maintain the pH of the aqueous phase of the product emerging from the reactor in the range of 8-9. The reaction temperature was 10° C. and the total average residence time was 2.5 hours. The reactor product was then introduced to a hydrolysis consisting of a continuous, back mixed reactor. The average residence time was 1.5 hours at 35° C. Sufficient sodium hydroxide was added as a 20% by weight solution to maintain the pH in the range of 7-10. The aqueous phase was separated at 35° C. in a continuous separator operated with a residence time of 0.5 hours. The organic phase from the separator was fed to a two stage continuous reactor operated at 35°-45° C. The total average residence time in the reactor was 4.5 hours. A 5 to 10% molar excess of ethylamine based on remaining unhydrolyzed cyanuric chloride derivatives was added as well as sufficient sodium hydroxide to maintain the pH of the aqueous phase of the reactor effluent in the range of 9-9.5. Crude atrazine product was analyzed by gas-liquid chromatography which gave the following composition.

| Component | Percent by Weight |
| --- | --- |
| 2-chloro-4-ethylamino-6-isopropylamino-s-triazine | 98.2 |
| 2-chloro-4,6-bis(ethylamino)-s-triazine | 0.3 |
| 2-chloro-4,6-bis(isopropylamino)-s-triazine | 1.0 |

ILLUSTRATIVE EMBODIMENT III

Using the apparatus and general procedure described in Illustrative Embodiment IA, a 30.5% by weight solution of cyanuric chloride in acetone was charged to a batch reaction vessel. A less than stoichiometric amount of isopropylamine (the molar ratio of cyanuric chloride to isopropylamine was 1.04) was charged over a period of one hour and then sufficient 20% by weight sodium hydroxide in water was added over a period of 40 minutes to bring the pH of the aqueous phase to 8.0. The temperature of the reaction mixture during both reaction steps was controlled at 10° C. Hydrolysis of the excess cyanuric chloride was effected by reducing the pH to 6.0 and heating the reaction mixture to 35° C. for a period of 0.5 hours. Aqueous sodium hydroxide solution was added as necessary to maintain the pH of the reaction mixture at 6.0. At the conclusion of this reaction step, the pH was increased to 8.0 and ethylamine as a 68% solution in water was added over a period of 30 minutes. Sufficient 20% by weight sodium hydroxide solution was added over a period of 45 minutes to produce a pH of 8.5. The temperature of the reaction mixture was maintained at 35° C. during this reaction sequence. Crude atrazine was isolated from the reaction mixture by precipitation with water. The molar yield of atrazine was 94.3% based on isopropylamine charged to the reaction. The composition of the crude atrazine was determined by gas-liquid chromatography and is given below.

| Compound | Composition % by weight |
| --- | --- |
| 2-chloro-4,6-bis(ethylamino)-s-triazine | 1.0 |
| 2-chloro-4,6-bis(isopropylamino)-s-triazine | 0.3 |
| 2-chloro-4-ethylamino-6-isopropylamino-s-triazine | 96.3 |

What is claimed is:

1. In the process for preparation of 2-chloro-4-ethylamino-6-isopropylamino-s-triazine by sequential reaction of cyanuric chloride with isopropylamine and ethylamine in the presence of an alkali metal hydroxide acid acceptor and a mixed acetone/water solvent system, the improvement which comprises; carrying out the initial reaction between cyanuric chloride and isopropylamine with at least a 4% molar excess over the stoichiometric amount of cyanuric chloride and subsequently treating the reaction product of this initial reaction with sufficient base to afford a pH in the reaction product of between about 6 and 11 thereby hydrolyzing excess cyanuric chloride present in the reaction product to a basic salt of monohydroxydichlorotriazine before the reaction product is passed to the second reaction stage.

2. The process according to claim 1 wherein the base employed is an alkali or alkaline earth metal hydroxide.

3. The process according to claim 2 wherein the base is an alkali metal hydroxide.

4. The process according to claim 3 wherein the pH of the reaction mixture is maintained between about 7 and about 10.

5. The process according to claim 4 wherein the base is sodium hydroxide.

6. The process according to claim 4 wherein the alkali metal hydroxide is added to the reaction product as an aqueous solution.

7. The process according to claim 1 wherein the hydrolysis reaction product is subject to phase separation to remove at least a portion of the basic salt of monohydroxydichlorotriazine as a component of the separated aqueous phase prior to passage of the reaction product to the second reaction stage.

* * * * *